United States Patent
Grubis et al.

(10) Patent No.: US 12,119,094 B2
(45) Date of Patent: Oct. 15, 2024

(54) SYSTEMS AND METHODS FOR CONNECTING DEVICES TO ELECTRONIC MEDICAL RECORDS

(71) Applicant: GE Precision Healthcare LLC, Wauwatosa, WI (US)

(72) Inventors: Matthew G. Grubis, New Berlin, WI (US); Stephen Treacy, Menomonee Falls, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 456 days.

(21) Appl. No.: 17/394,625

(22) Filed: Aug. 5, 2021

(65) Prior Publication Data
US 2023/0043365 A1 Feb. 9, 2023

(51) Int. Cl.
*G16H 10/60* (2018.01)
*G16H 40/67* (2018.01)

(52) U.S. Cl.
CPC ............. *G16H 10/60* (2018.01); *G16H 40/67* (2018.01)

(58) Field of Classification Search
CPC ............................... G16H 10/60; G16H 40/67
See application file for complete search history.

(56) References Cited

U.S. PATENT DOCUMENTS

| 8,001,235 | B2* | 8/2011 | Russ | H04L 67/12 |
| | | | | 709/224 |
| 11,816,771 | B2* | 11/2023 | Muhsin | G16H 40/63 |
| 11,924,282 | B2* | 3/2024 | Durrant | H04L 5/14 |
| 2010/0169121 | A1* | 7/2010 | Herbst | G06Q 10/10 |
| | | | | 705/2 |
| 2015/0363563 | A1* | 12/2015 | Hallwachs | G16H 40/67 |
| | | | | 705/3 |
| 2018/0082036 | A1* | 3/2018 | Hanrahan | H04L 65/762 |
| 2019/0320898 | A1* | 10/2019 | Dirghangi | A61B 3/156 |
| 2019/0371456 | A1* | 12/2019 | Page | G16H 10/60 |

(Continued)

FOREIGN PATENT DOCUMENTS

KR 101807574 B1 * 12/2017

OTHER PUBLICATIONS

A. Kliem, A. Boelke, A. Grohnert, N. Traeder, "A Reconfigurable Middleware for On-demand Integration of Medical Devices", 2016, IRBM, vol. 37, Issue 4, pp. 198-209, doi.org/10.1016/j.irbm.2016.05.003. (Year: 2016).*

(Continued)

*Primary Examiner* — Jason S Tiedeman
*Assistant Examiner* — Malak M Nasser
(74) *Attorney, Agent, or Firm* — Andrus Intellectual Property Law, LLP

(57) ABSTRACT

A method for connecting devices to a health record configured to have a single connection thereto. The method includes creating a virtual device and configuring the virtual device such that two or more of the devices are connectable thereto. The virtual device receives data from each of the two or more of the devices and aggregates the data from each of the two or more of the devices into aggregate data. The aggregate data is associated with the virtual device as originating therefrom. The method further includes connecting the virtual device to the electronic medical record as the single connection thereto and providing the aggregate data from the virtual device to the health record.

20 Claims, 4 Drawing Sheets

(56) References Cited

U.S. PATENT DOCUMENTS

| | | | |
|---|---|---|---|
| 2021/0057059 A1* | 2/2021 | Chahal | G16H 40/20 |
| 2021/0304881 A1* | 9/2021 | White | G16H 40/20 |
| 2022/0101968 A1* | 3/2022 | Lancelot | G06F 21/6245 |
| 2022/0262508 A1* | 8/2022 | Bajwa | A61N 1/37282 |
| 2022/0336099 A1* | 10/2022 | Butka | A61B 5/748 |
| 2022/0406460 A1* | 12/2022 | Golan | G16H 50/20 |
| 2023/0157544 A1* | 5/2023 | Gross | G16H 10/60 |
| | | | 600/301 |

OTHER PUBLICATIONS

S Rubí JN, L Gondim PR. "IoMT Platform for Pervasive Healthcare Data Aggregation, Processing, and Sharing Based on OneM2M and OpenEHR", Oct. 3, 2019; Sensors (Basel), 19(19):4283. doi: 10.3390/s19194283. (Year: 2019).*

A. King et al., "An open test bed for medical device integration and coordination," 2009, 31st International Conference on Software Engineering—Companion Volume, Vancouver, BC, Canada, 2009, pp. 141-151, doi: 10.1109/ICSE-Companion.2009.5070972. (Year: 2009).*

KR 101807574 B1 (Machine Translation) (Year: 2017).*

Vital Sync Virtual Patient Monitoring Platform-User Guide—20 pages. MedTronic. 2015.

\* cited by examiner

US 12,119,094 B2

SYSTEMS AND METHODS FOR CONNECTING DEVICES TO ELECTRONIC MEDICAL RECORDS

FIELD

The present disclosure generally relates to systems and methods for connecting devices to medical records, and more particularly to electronic medical records limited to having a single connection thereto.

BACKGROUND

Contemporary patient care and monitoring often involves the use of a device to acquire psychological information for a patient. This device is frequently connected in a manner to communicate with a health record, such as an electronic medical record (EMR) system, which maintain a record of the patient's medical history over time. Patient monitoring systems presently known in the art are "monitor-based" such that a patient is admitted to a specific device. For example, a given patient may initially be admitted to a ventilator device in an intensive care unit (ICU). This ventilator may then be connected to the EMR to maintain an accurate and comprehensive record of the patient and the patient's medical history. The patient may later be transferred to a standard room outside the ICU, whereby the EMR will instead be connected to a heart rate monitor, for example.

An exemplary EMR presently known in the art is Cerner Millennium CareAware interface.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One example according to the present disclosure generally relates to a method for connecting devices to a health record configured to have a single connection thereto. The method includes creating a virtual device and configuring the virtual device such that two or more of the devices are connectable thereto. The virtual device receives data from each of the two or more of the devices and aggregates the data from each of the two or more of the devices into aggregate data. The aggregate data is associated with the virtual device as originating therefrom. The method further includes connecting the virtual device to the electronic medical record as the single connection thereto and providing the aggregate data from the virtual device to the health record.

In certain examples, at least one of the devices is a real device.

In certain examples, the virtual device is configured to be associated with a patient.

In certain examples, the data from the devices is provided to the electronic medical record in real-time.

In certain examples, the two or more devices are simultaneously connected to the virtual device and include a ventilator and a pulse oximeter each receiving the data from a common patient.

In certain examples, the virtual device has an identity, and the identity is associated with a physical location in which the devices are located. In further examples, the physical location is a bed location in a medical facility.

In certain examples, the electronic medical record operates via HL7 protocol.

In certain examples, the virtual device is configured such that individual devices within the devices are connectable and disconnectable thereto without disconnecting the virtual device from the electronic medical record.

In certain examples, the virtual device is one of a pool of available virtual devices selectable for connecting to the electronic medical record.

Another example according to the present disclosure generally relates to a system for monitoring data from devices. The system includes an electronic medical record configured to have a single connection thereto. A virtual device is configured to connect to two or more of the devices, where the two or more of the devices are real devices each providing data to the virtual device, and where the virtual device aggregates the data from each of the two or more of the devices into aggregate data, the aggregate data being associated as originating with the virtual device. The virtual device is selectable from a pool of virtual devices to be the single connection to the electronic medical record. The aggregate data is provided from the virtual device for monitoring.

In certain examples, the virtual device is configured to be associated with a patient.

In certain examples, the patient data from the devices is provided to the electronic medical record in real-time.

In certain examples, the two or more devices are simultaneously connected to the virtual device and include a ventilator and a pulse oximeter each receiving the data from a common patient.

In certain examples, the virtual device has an identity associated with a physical location in which the devices are located. In further examples, the physical location is a bed location in a medical facility.

In certain examples, the electronic medical record operates via HL7 protocol.

In certain examples, the virtual device is configured such that individual devices within the devices are connectable and disconnectable without disconnecting the virtual device from the electronic medical record.

In certain examples, the virtual device has an identity that is based other than on the patient and the devices.

Another example according to the present disclosure generally relates to a method for connecting medical devices receiving data comprising clinical data and device telemetry data from a common patient to an electronic medical record configured to have a single connection thereto. The method includes creating a pool of virtual devices and configuring individual virtual devices within the pool of virtual devices such that the medical devices are connectable thereto simultaneously. The method further includes associating the patient with one of the individual virtual devices and selecting the one of the individual virtual device for connecting to the electronic medical record as the single connection thereto, where the one of the individual virtual device is configured such that individual medical devices within the medical devices are connectable and disconnectable thereto without disconnecting the one of the individual virtual devices from the electronic medical record, and where the one of the individual virtual devices aggregates the data from the individual medical devices connected thereto into aggregate data. The method further includes providing the aggregate data in real-time from the one of the individual virtual devices to the electronic medical record.

Various other features, objects and advantages of the disclosure will be made apparent from the following description taken together with the drawings.

BRIEF DESCRIPTION OF THE DRAWINGS

The present disclosure is described with reference to the following drawings.

DETAILED DISCLOSURE

Figure 1:
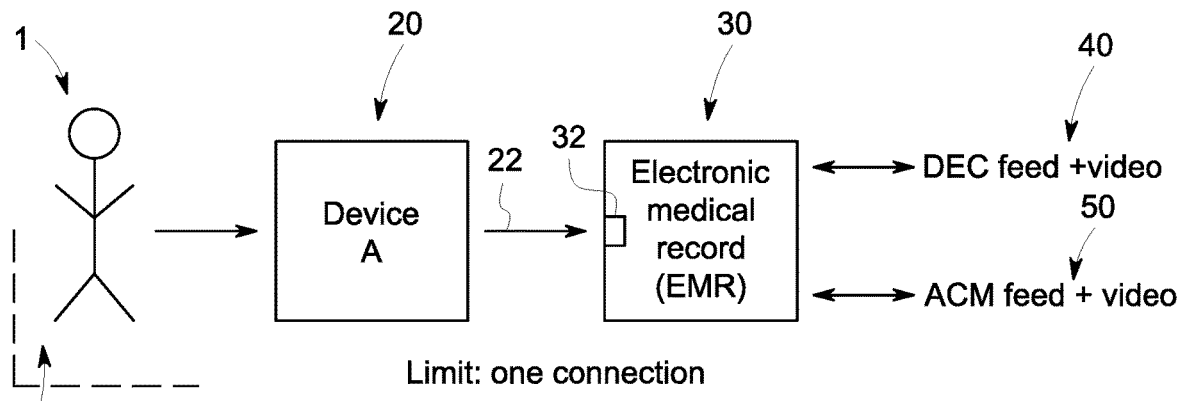
FIG. 1 is a schematic depicting a system for monitoring patient data from devices as presently known in the art.

The present inventors have recognized that in contemporary patient care, multiple devices are often used simultaneously to acquire and/or monitor different physiological information for a given patient. In addition to having varying types of devices available for use, the number and specific identities of devices used for a given patient may change over the duration of care. Likewise, the patient's situation or care plan may change throughout a hospital visit, for example.

However, electronic medical records (EMRs) presently known in the art are typically configured to be monitor based. In other words, some EMRs are limited where all monitoring devices are defined at the installation of the system. A single predefined device is connected to the patient, which provides a consistent device identity to the EMR, as expected by the EMR. The Internet of Medical Things (IoMT) paradigm breaks this legacy model by embracing the concept of many individual "Medical Things" transiently applied and removed from the patient to adjust to the patient's condition. There is no single, predefined device that is considered as the consistent device identity. Thus, not only are EMRs currently limited to being connected to a single device at a time, but they require the additional step of disconnecting from a first device before a second device may be connected. This limits the ability of the EMR to have a complete and comprehensive view of data associated with the patient, and also renders the process for changing medical devices as patient needs evolve cumbersome and prone to errors. Moreover, since the medical devices to which the patients are admitted are often identified by physical location (e.g., a ventilator in ICU room E6), even transferring the patient to a different location within the facility (e.g., a standard room) becomes laborious.

To this end, the present inventors have recognized that it would be advantageous for patient monitoring systems to be "patient-based," whereby the patient is admitted to an ecosystem or a given facility, for example, rather than to a particular medical device. For example, the patient may be admitted within the EMR to a particular hospital. In this manner, individual medical devices could be associated and disassociated from the patient without changing the patients admission to the given facility.

Unfortunately, the present inventors have further recognized that EMRs presently known in the relevant art are not presently capable of functioning in this patient-based model. One such EMR presently known in the art is the Cerner Millennium CareAware interface (others include those sold by Epic, Medtronic, and All Scripts, for example). The CareAware interface operates using the HL7 clinical document architecture standard and is limited to having a single incoming connection. In other words, the CareAware interface and other EMRs presently known in the art were designed to be monitor-based since only a single device (such as a ventilator or pulse oximeter) can be connected to the EMR at a given time. As discussed above, this requires the patient to be admitted to a specific device, as that one specific device is the only connection to the EMR. In this example, when the patient is no longer in need of a ventilator or pulse oximeter, the prior art configurations require that the patient and device be removed from the EMR, whereby the patient can be admitted to a different device for connection to the EMR.

It should be recognized that while the present disclosure generally describes the output of the virtual devices described herein as being provided to an EMR, any recipient or consumer of the data originating with medical devices is contemplated. For example, the output of a virtual device according to the present disclosure may be a third-party application or device that does not store such data, but further communicates or displays this data (or a derivative thereof). Historically, this class of devices are not predefined to the EMR, and thus require proxy devices to communicate information to the EMR (since they are not connected to a communication network themselves). These types of devices are exemplified by commercially available devices such as the GE CARESCAPE V100 Vital Signs Monitor, Welch Allyn 300 Series Vital Signs Monitor, and the Covidien Puritan Bennett Ventilators.

FIG. 1 depicts an exemplary configuration of EMR 30 and device 20 connections as presently known in the art. A patient 1 within a physical location 2 (such as a bed location, room, or ward of a medical facility) is connected to a device 20 in a manner presently known in the art. As discussed above, exemplary devices 20 include ventilators and pulse oximeters, as well as those for electrocardiogram (ECGs), electromyograms (EMGs), electroencephalograms (EEGs), blood pressure sensors, anesthesia devices, thermometers, or respiratory sensors, for example. In certain examples, these devices 20 are "Internet of Medical Things" devices. The electronic medical record (EMR) 30 of FIG. 1 operates under the HL7 clinical document architecture standard or another limited to a single connection thereto.

As such, one device 20 is connected to the EMR 30 at a single incoming connection 32 and transmits data 22 thereto in real-time. It should be recognized that the data 22 provided to the EMR 30 corresponds to the type of device 20 connected thereto. For example, in the case of a pulse oximeter as the particular type of device 20, the data 22 may include such clinical data as a heart rate and oxygen saturation level produced in a manner known in the art. Other examples of clinical data include blood pressure (e.g., non-invasive systolic and diastolic blood pressure), glucose and/or various protein levels. Additionally, the data 22 is not limited to clinical data, but may also include device telemetry data, such as indications of having a low battery, an overheat condition, disconnected leads, communication errors or signal artifacts. The EMR 30 may then output a DEC feed 40 (e.g., which may include patient vital signs data such as SpO2, pulse rate, and respiratory rate, and/or a ACM video 50 (e.g., which may include alarm conditions such as high or low heart rate, high or low SpO2 level, and high or low respiratory rate) in a matter in the art. In short, DEC and ACM feeds represent the standardized Health Level 7 (HL7), Integrating the Healthcare Enterprise® (IHE), Point-of-care (PCD), Device Enterprise Communication (DEC) and Alarm Communication Management (ACM) protocols respectively.

Figure 2:
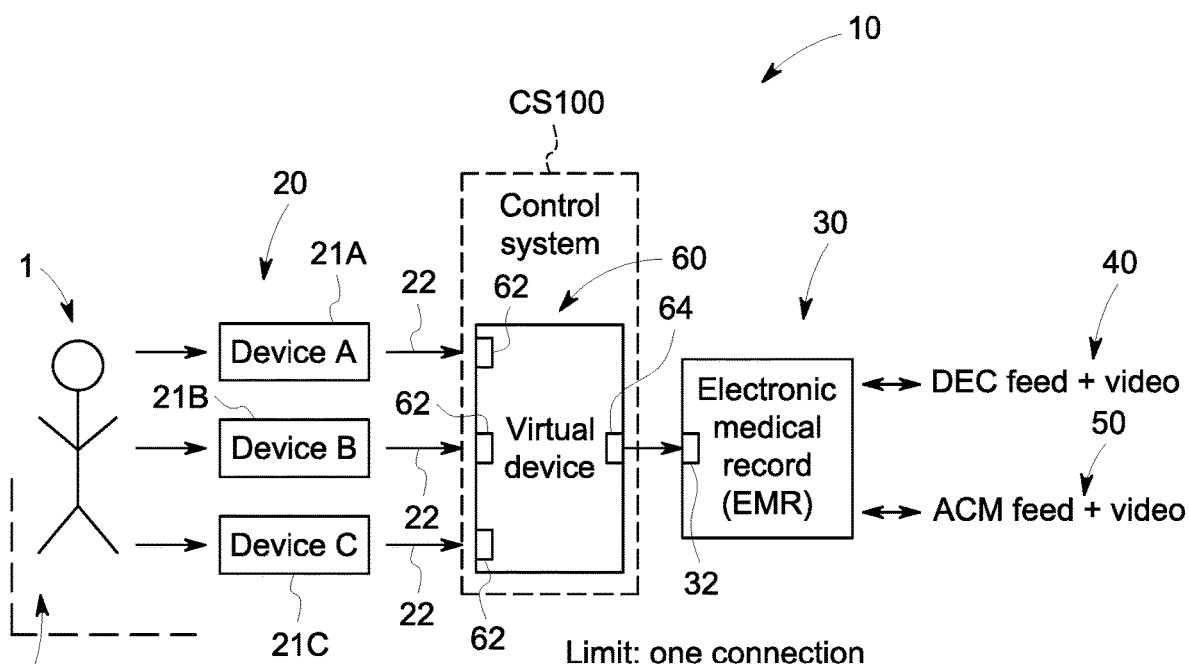
FIG. 2 is a schematic depicting an exemplary system for monitoring patient data from devices according to the present disclosure.

Through experimentation and development, the present inventors have identified a new mechanism by which a legacy EMR 30 such as the Cerner Millennium CareAware interface operating on the HL7 clinical document architecture standard functionally operate with multiple devices 20, notwithstanding the inherent limitation of having only a single incoming connection 32. In particular, the present inventors have developed a virtual device 60 that may be connected to the single incoming connection 32 of the EMR 30, while itself permitting dynamic adding and subtracting of multiple devices 20 thereto. In the exemplary system 10 shown in FIG. 2, the devices 20 include multiple individual devices 21A-21C, each providing data 22 to the virtual device 60. In particular, the virtual device 60 is configured to have multiple incoming connections 62, which are theoretically unlimited in number. Only a single outgoing connector 64 is required, which corresponds to the single incoming connection 32 of the EMR 30, thereby providing a connection by which data may flow between the virtual device 60 and the EMR 30. A DEC feed 40 and/or ACM feed 50 may also be provided in conjecture with the EMR 30 in a customary manner.

A control system CS100 (discussed further below), which in certain examples is entirely embodied as the virtual device 60) is responsible for managing communication with all the devices 21A-21C, including any protocol and data model translation into a common internal representation. The virtual device 60 itself may produce new physiological information algorithmically from data received from devices 21A-21C. Devices 21A-21C represent transiently applied, possibly wireless, possibly single-use IoMT physiological sensors or acquisition elements. The virtual device 60 holistically combines these independent physiological elements by managing a dynamic association between unique device identifiers, unique patient identifiers and a unique location identifiers. The virtual device 60 is uniquely designed to handle the transient nature and dynamic behavior of the plethora of devices 21A-21C.

During configuration of the system 10, a pool of virtual devices 60, are programmatically defined to be a set of static, well-known identifiers shared with the EMRs configuration. The virtual devices 60 have a static unique identifier and may be bound to represent a specific bed location in the hospital (ICU Bed 4A as an example). During the admission of a patient the virtual device 60, which is aware of the patients actual assigned bed and current set of IoMT devices, reserves a pre-established virtual device 60 from the pool of defined virtual devices 60. The virtual device 60 is then defined to represent that particular patient, including associating any patient identifier (Name, DoB, MRN, Visit Number, etc.) and current bed location for the duration of their admission to the system. The virtual device 60 leverages the configured information to communicate to the EMR 30 on behalf of the patient. The virtual device provides a consistent device identifier to the EMR 30, even though the actual plurality of transient IoMT devices may be dynamically applied and removed. There is no limit on the number of actual IoMT devices which are represented to the EMR by a single virtual device. At the conclusion of the patient monitoring session, the virtual device 60 is discharged and returned to the pool of available virtual devices for any new patients who will be admitted in the future In certain examples, the data 22 received from the devices 20 is aggregated within the virtual device 60 into a single set of aggregate data. In this manner, the output (the aggregate data) of the virtual device 60 to the EMR 30 via the single outgoing connector 64 appear as if it relates to, or originates from, the virtual device 60 itself. In other words, if one of the devices 20 provides data 22 to the virtual device 60 indicating a low battery state, for example, the virtual device 60 will appear to the EMR 30 as if the virtual device 60 itself has a low battery (despite not having any batteries). In this manner, the system 10 may be configured such that the EMR 30 sees only virtual device 60, which itself appears to be the original source of all of the data 22 received by all of the devices 20 connected thereto, now combined into a single, aggregated set of data.

Figure 3:
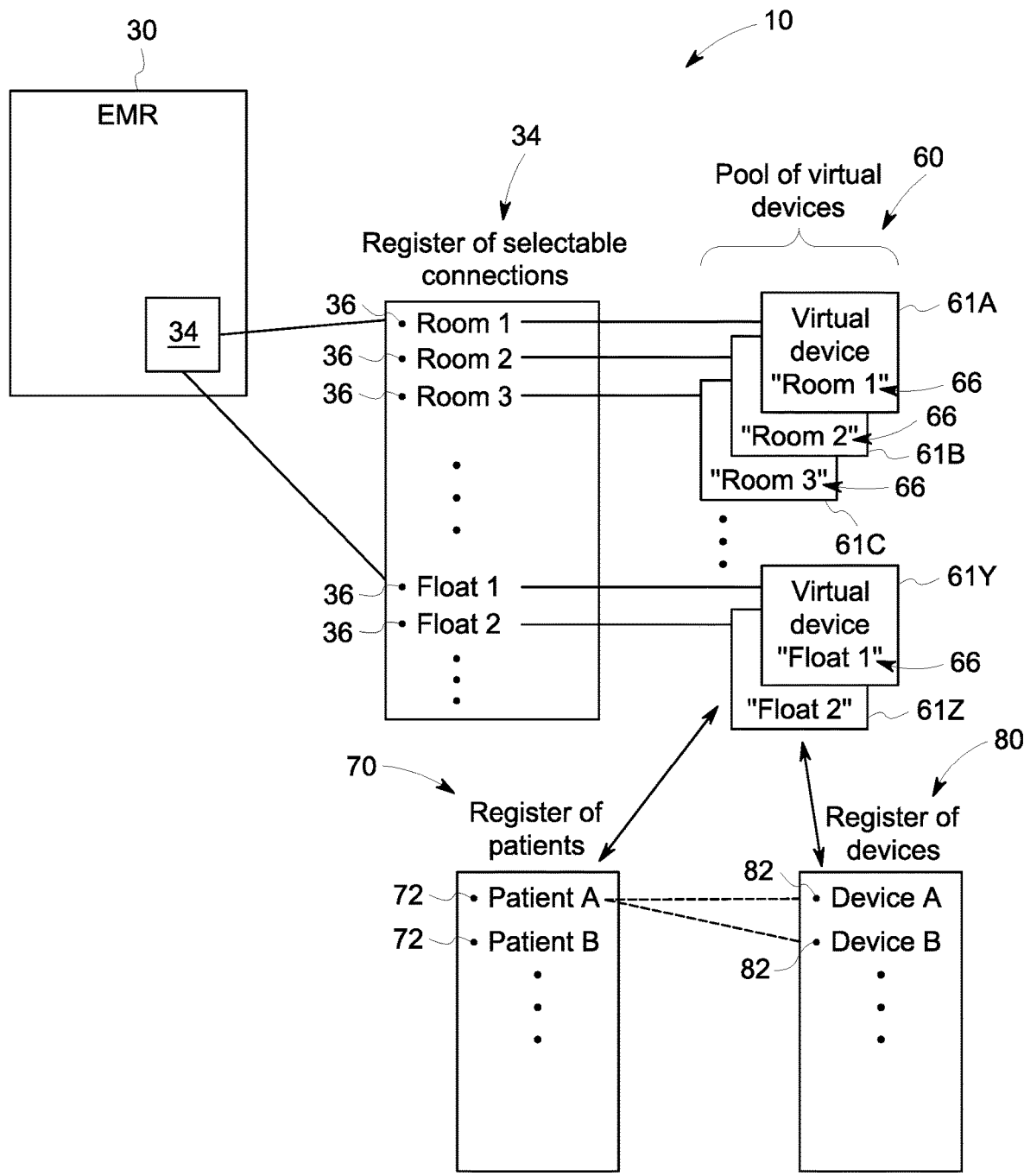
FIG. 3 is a schematic depicting an exemplary data structure for communicating between devices and the electronic medical record in the system of FIG. 2.

FIG. 3 depicts an exemplary data structure used for communicating between the virtual devices 60 and the EMR 30 within a system 10 according to the present disclosure. The EMR 30 includes or is configured to access a register of selectable connections 34 in a manner presently known in the art. The register of selectable connections 34 (as well as a pool of virtual devices 60, register of patients 70, and/or register of devices 80 discussed below) may be stored in a memory system accessible by the EMR 30, for example, as discussed further below. However, in contrast to the system of FIG. 1 as presently know in the art, the register of selectable connections 34 refers to a listing of a pool of virtual devices 6, rather than listing out the devices 20 directly (as in the system of FIG. 1). As discussed above, each of the virtual devices 60 acts as a middle-person between the devices 20 and the EMR 30.

In this manner, the system 10 presently shown permits the register of selectable connections 34 to be much shorter than listing out all devices contained within a given facility that could potentially be used with a patient (which may number in the thousands for a given hospital, for example). The system 10 may also be configured to assess the location or region of a facility in which the EMR 30 is being accessed before populating the register of selectable connections 34, thereby showing only local, relevant virtual devices 60 that are reasonable for selection. In other words, when accessing the EMR 30 from a cardiac care wing, virtual devices 60 associated with obstetrics may be excluded from the register of selectable connections 34. Similarly, if a pediatric patient has been selected (in the process described below), the register of selectable connections 34 may be limited to showing only virtual devices 60 associated with pediatric patients (and likewise, the register of devices 80 discussed below limited to those compatible with pediatric patients). It should be recognized that by incorporating the intelligence in pairing patients 1, virtual devices 60, and devices 20, the presently disclosed system 10 may also serve as a safeguard for using effective and appropriate equipment approved for a given patient and circumstance.

In the example shown in FIG. 3, the EMR 30 is configured such that the register of selectable connections 34 includes individual selections 36 labeled to correspond to a physical location 2 of the patient 1 (for example rooms 1-3), whereas other individual selections 36 are labeled as "Float 1" and "Float 2", which are intended to not be tied to any particular location. In other words, some of the individual selections 36 correspond to virtual devices 60 that are not associated with a room, but are instead customarily used in a transient manner. For example, individual selections 36 labeled as "float" may be those associated with patients who are ambulatory, rather than those physically connected to a ventilator in the ICU. "Float" labeled virtual devices 60 may also be used for patients 1 that do not typically stay in one place for a long time, for example used with patients within the emergency room that will quickly be moved elsewhere.

With continued reference to the example shown in FIG. 3, the individual selections 36 within the register of selectable connections 34 of the EMR 30 are associated with individual virtual devices 61A-61C among the virtual devices 60. As can be seen, the individual virtual devices 61A-61C have corresponding identities 66 that allow the individual virtual devices 61A-61C to be distinctly identified apart from one another, which here is shown within the register of selectable connections 34 for selection. In this manner, each of the virtual devices 60 presently disclosed are selectable by a legacy EMR 30 to form a single connection thereto (via the single incoming connection 32 presently known in the art).

Each of the virtual devices 60 presently disclosed is itself configured to be connectable or associated with a broad number and wide variety of devices, as well as to be associated with specific patients coming and going throughout a facility. In certain examples, EMRs known in the art use a unique patient identifier to identify a given patient, such a medical record number or social security number.

Each of the virtual devices 60 is provided in communication with a register of devices 80, which includes a listing of individual entries 82. The individual entries 82 are each associated with a particular device 20, for example a ventilator or arterial blood pressure device. As discussed above, the virtual devices 60 allow the particular devices 20 to be added thereto or removed therefrom by selection and deselection of the individual entries 82 associated with a given virtual device 60 to a given virtual device 60.

The virtual device 60 is also provided in communication with a register of patients 70, which includes individual entries 72 associated with each of the patients in the facility. For example, hospitals in the U.S. typically use an admit/discharge transfer (ADT) system to manage patient admissions, which may be part of the EMR or an interface within the ADT system. In this manner, any number of devices 20 within the register of devices 80 can be associated with a virtual device 60 that is also associated with the selected one of the patients in the register of patients 70. The virtual device 60 then manages and combines all of the data received from the selected devices from the register of devices 80 and presents this data via the single incoming connection 32 to the EMR 30 in the manner described above.

Figure 4:
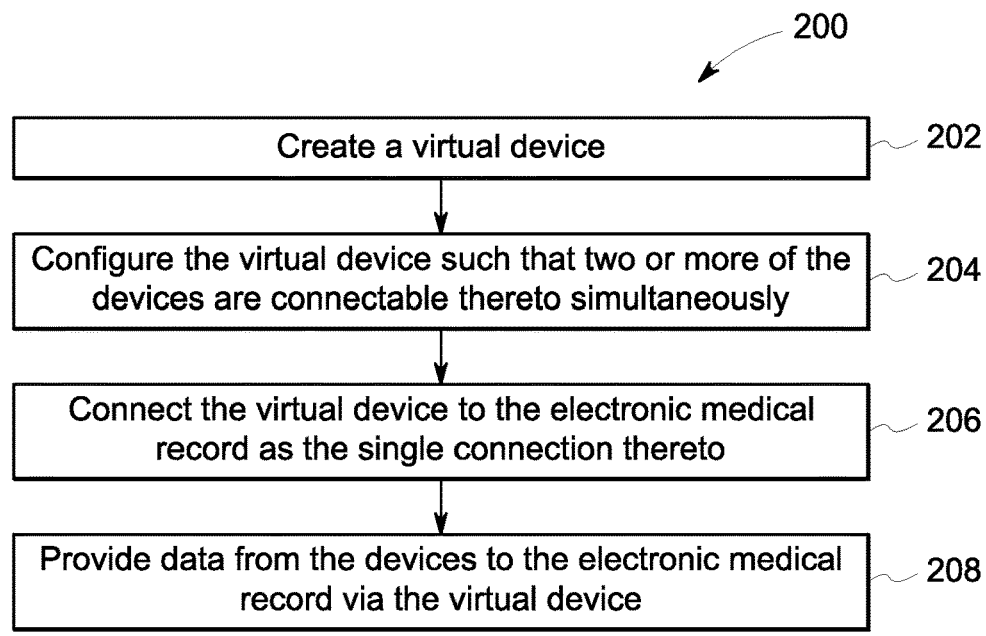
FIG. 4 is a process for an exemplary method for connecting devices to electronic medical records according to the present disclosure.

FIG. 4 provides an exemplary method 200 for connecting devices to an electronic medical record having a single connection according to the present disclosure. Step 202 begins with creating a virtual device, and configuring the virtual device such that two or more devices are connectable thereto simultaneously in step 204. As discussed above, these devices to be simultaneously connected to the virtual device may include medical devices such as a thermometer or a heart rate sensor, for example. Step 206 provides for connecting the virtual device to the electronic medical record as a single connection thereto, which enables the use of legacy EMRs despite the present identified desire of simultaneously operating multiple devices in conjunction with a single patient. Finally, step 208 provides for a providing data from the devices to the electronic medical record via the virtual device.

Figure 5:
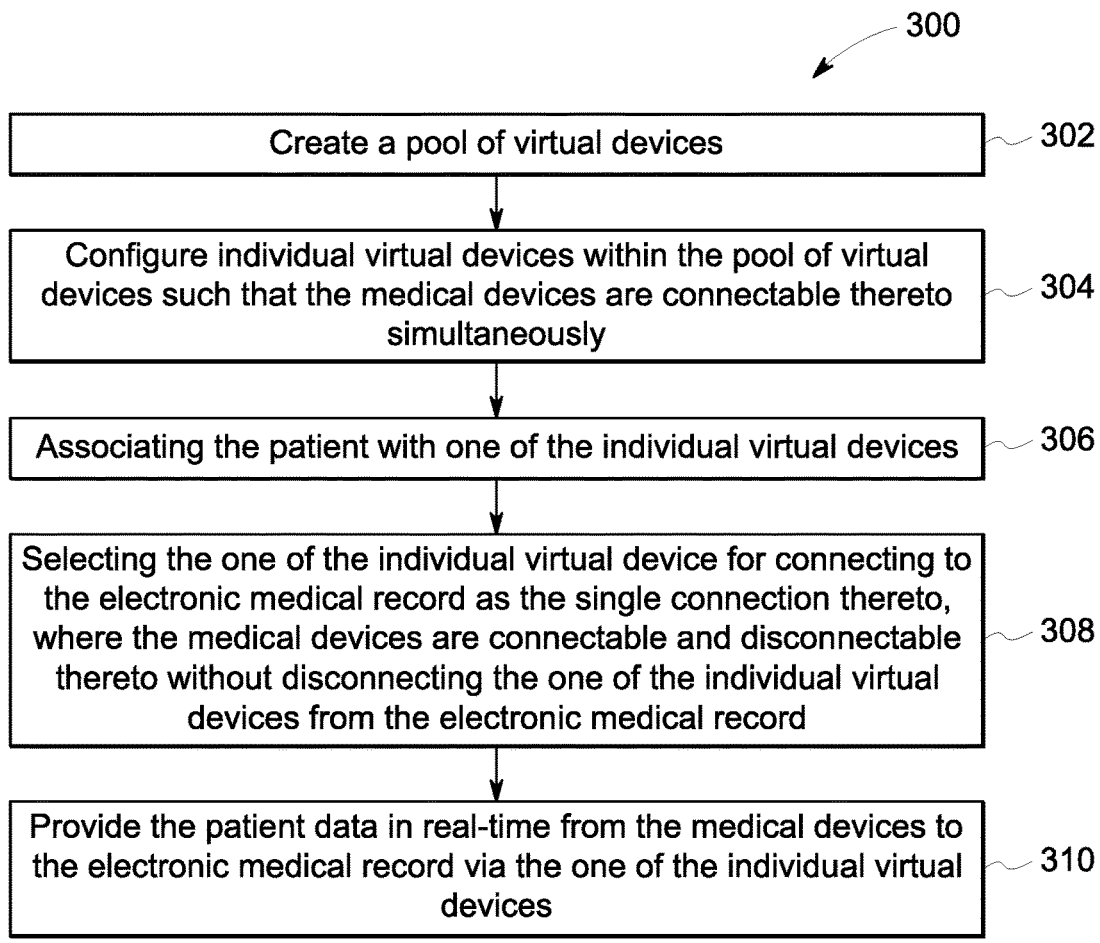
FIG. 5 is a process for another exemplary method for connecting devices to electronic medical records according to the present disclosure.

FIG. 5 depicts an alternative method 300 for connecting devices to an electronic medical record and a single connection thereto according to the present disclosure. Step 302 provides for creating a pool of virtual devices, which as discussed above may be selectable based on the location and/or care plan of the patient. For example, some of the virtual devices may be associated with a patient room or a ward within a medical facility, whereas others are designated as floaters configured to move about with the patient, including following the patient home, for example. Step 304 provides for configuring individual virtual devices within the pool of virtual devices such that medical devices are connectable to each of the individual virtual devices simultaneously. Step 306 provides for associating the patient with one of the individual virtual devices, and then in step 308 selecting one of the individual virtual devices for connecting to the electronic medical record as the single connection thereto. Additionally, the medical devices are connectable and disconnectable from one of the individual virtual devices without disconnecting the one of the individual virtual devices from the electronic medial record. Finally, step 310 provides for providing the patient data from the medical devices in real time to the electronic medical record via the one of the individual virtual devices.

Figure 6:
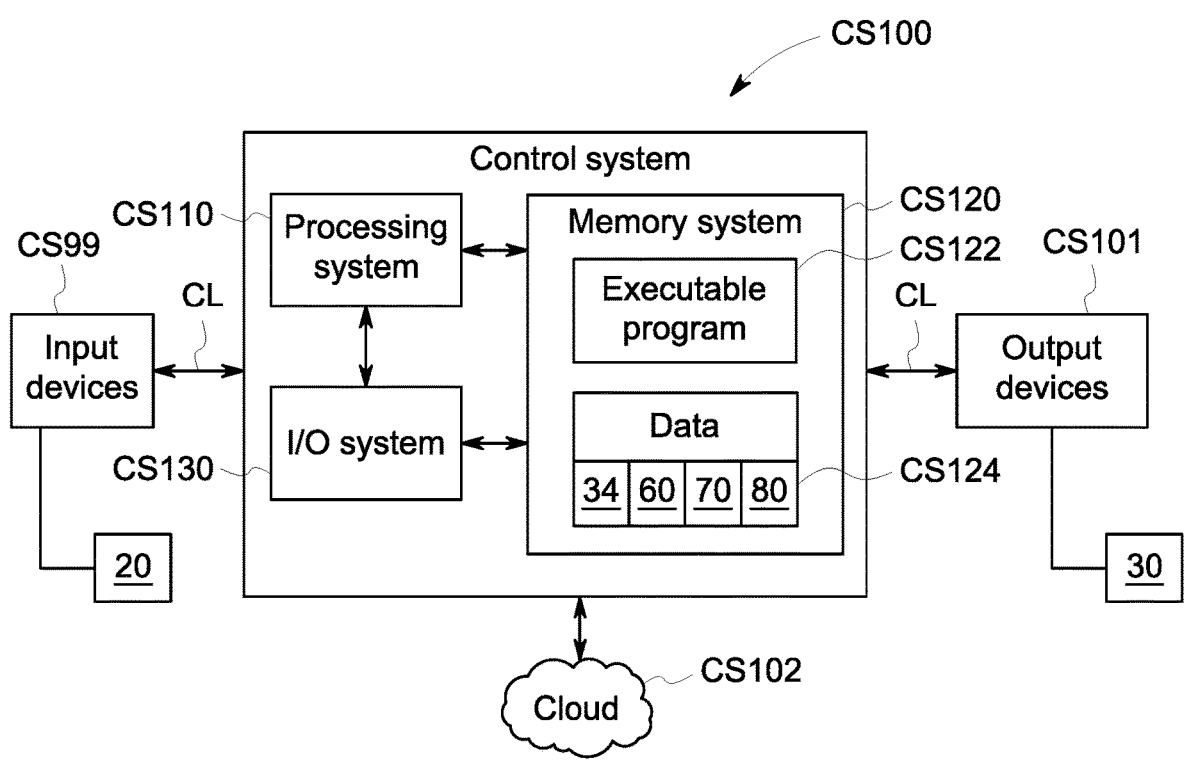
FIG. 6 is a schematic for an exemplary control system such as may be used within the system at FIG. 2.

FIG. 6 discloses an exemplary control system CS100 such as may be incorporated within the system 10. The control system CS100 may communicate with the virtual devices 60, and/or the virtual devices 60 may be stored within data CS124 of the control system CS100. Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

In certain examples, the control system CS100 communicates with each of the one or more components of the system 10 via a communication link CL, which can be any wired or wireless link. The control module CS100 is capable of receiving information and/or controlling one or more operational characteristics of the system 10 and its various sub-systems by sending and receiving control signals via the communication links CL. It will be recognized that the extent of connections and the communication links CL may in fact be one or more shared (virtual or and/or physical) connections, or links, among some or all of the components in the system 10. Moreover, the communication link CL lines are meant only to demonstrate that the various control elements are capable of communicating with one another, and do not represent actual wiring connections between the various elements, nor do they represent the only paths of communication between the elements. Additionally, the system 10 may incorporate various types of communication devices and systems, and thus the illustrated communication links CL may in fact represent various different types of wireless and/or wired data communication systems.

The control system CS100 may be a computing system that includes a processing system CS110, memory system CS120, and input/output (I/O) system CS130 for communicating with other devices, such as input devices CS99 and output devices CS101, either of which may also or alternatively be stored in a cloud CS102. The processing system CS110 loads and executes an executable program CS122 from the memory system CS120, accesses data CS124 stored within the memory system CS120, and directs the system 10 to operate as described in further detail below.

The processing system CS110 may be implemented as a single microprocessor or other circuitry, or be distributed across multiple processing devices or sub-systems that cooperate to execute the executable program CS122 from the memory system CS120. Non-limiting examples of the processing system include general purpose central processing units, application specific processors, and logic devices.

The memory system CS120 may comprise any storage media readable by the processing system CS110 and capable of storing the executable program CS122 and/or data CS124. The memory system CS120 may be implemented as a single storage device, or be distributed across multiple storage devices or sub-systems that cooperate to store computer readable instructions, data structures, program modules, or other data. The memory system CS120 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for connecting medical devices to a health record configured to have only a single incoming connection thereto, the method comprising:

creating a virtual medical device comprising software that mimics a single medical device configured to produce medical data;

configuring the virtual medical device such that two or more of the actual medical devices are connectable thereto, wherein the virtual medical device receives data from each of the two or more of the actual medical devices, wherein the virtual medical device aggregates the data from each of the two or more of the actual medical devices into aggregate data, the aggregate data being associated with the virtual medical device as originating therefrom as the single medical device;

connecting the virtual medical device to the health record as the only single incoming connection thereto; and providing the aggregate data from the virtual medical device to the health record.

2. The method according to claim 1, wherein at least one of the two or more actual medical devices is a physical device.

3. The method according to claim 1, wherein the virtual medical device is configured to be associated with a patient.

4. The method according to claim 1, wherein the aggregate data is provided to the health record in real-time.

5. The method according to claim 1, wherein the two or more actual medical devices simultaneously connected to the virtual medical device include a ventilator and a pulse oximeter each associated with a common patient.

6. The method according to claim 1, wherein the virtual medical device has an identity, and wherein the identity is associated with a physical location in which the devices are located.

7. The method according to claim 6, wherein the physical location is a bed location in a medical facility.

8. The method according to claim 1, wherein the health record comprises an electronic medical record that operates via HL7 protocol.

9. The method according to claim 1, wherein the virtual medical device is configured such that individual actual medical devices within the actual medical devices are connectable and disconnectable thereto without disconnecting the virtual medical device from the health record.

10. The method according to claim 1, wherein the virtual medical device is one of a pool of available virtual medical devices selectable for connecting to the health record.

11. A system for monitoring data from actual medical devices, the system comprising:

an electronic medical record configured to have only a single incoming connection thereto;

a control system comprising a processing system; and a virtual medical device comprising software executable by the processing system such that the virtual medical device mimics a single medical device configured to produce medical data, the virtual medical device being configured to connect to two or more of the actual medical devices, wherein the two or more of the actual medical devices are physical devices each providing data to the virtual medical device, wherein the virtual medical device aggregates the data from each of the two or more of the actual medical devices into aggregate data, the aggregate data being associated as originating with the virtual medical device as the single medical device, and wherein the virtual medical device is selectable from a pool of virtual medical devices to be the only single incoming connection to the electronic medical record;

wherein the aggregate data is provided from the virtual medical device for monitoring.

12. The system according to claim 11, wherein the virtual medical device is configured to be associated with a patient.

13. The system according to claim 11, wherein the data from the two or more actual medical devices is provided to an electronic medical record and includes both clinical data and device telemetry data.

14. The system according to claim 11, wherein the two or more actual medical devices are simultaneously connected to the virtual medical device and include a ventilator and a pulse oximeter each receiving the data from a common patient.

15. The system according to claim 11, wherein the virtual medical device has an identity, and wherein the identity is associated with a physical location in which the devices are located.

16. The system according to claim 15, wherein the physical location is a bed location in a medical facility.

17. The system according to claim 11, wherein the aggregate data is provided to an electronic medical record that operates via HL7 protocol.

18. The system according to claim 11, wherein the virtual medical device is configured such that individual actual medical devices within the two or more actual medical devices are connectable and disconnectable without disconnecting the virtual medical device from the electronic medical record.

19. The system according to claim 11, wherein the virtual medical device has an identity, and wherein the identity is based other than on the patient and the devices.

20. A method for connecting actual medical devices receiving data comprising clinical data and device telemetry data from a common patient to an electronic medical record configured to have only a single incoming connection thereto, the method comprising:

creating a pool of virtual medical devices each comprising software that mimics a single medical device;

configuring individual virtual medical devices within the pool of virtual medical devices such that the actual medical devices are connectable thereto simultaneously;

associating the patient with one of the individual virtual medical devices;

selecting the one of the individual virtual medical device for connecting to the electronic medical record as the only single incoming connection thereto, wherein the one of the individual virtual medical device is configured such that individual actual medical devices within the actual medical devices are connectable and disconnectable thereto without disconnecting the one of the individual virtual medical devices from the electronic medical record, wherein the one of the individual virtual medical devices aggregates the data from the individual medical devices connected thereto into aggregate data, the aggregate data being associated with the one of the individual virtual medical device as originating therefrom as the single medical device; and providing the aggregate data in real-time from the one of the individual virtual medical devices to the electronic medical record.

* * * * *